(12) United States Patent
Baker et al.

(10) Patent No.: US 7,625,885 B2
(45) Date of Patent: Dec. 1, 2009

(54) CYTOTOXIN COMPOUND AND METHOD OF ISOLATION

(75) Inventors: Bill J Baker, Tampa, FL (US); Thusahara Diyabalanage, Tampa, FL (US); James B McClintock, Birmingham, AL (US); Charles D Amsler, Pelham, AL (US)

(73) Assignees: University of South Florida, Tampa, FL (US); The UAB Research Foundation, Birmingham, AL (US)

( * ) Notice: Subject to any disclaimer, the term of this patent is extended or adjusted under 35 U.S.C. 154(b) by 280 days.

(21) Appl. No.: 10/906,386

(22) Filed: Feb. 17, 2005

(65) Prior Publication Data

US 2005/0187286 A1    Aug. 25, 2005

Related U.S. Application Data

(60) Provisional application No. 60/521,073, filed on Feb. 17, 2004.

(51) Int. Cl.
*A61K 31/585* (2006.01)
*A61K 31/665* (2006.01)

(52) U.S. Cl. .................................... 514/175; 514/99

(58) Field of Classification Search ........................ None
See application file for complete search history.

(56) References Cited

U.S. PATENT DOCUMENTS

| | | | | |
|---|---|---|---|---|
| 5,324,739 A * | 6/1994 | Gerwick et al. | ............. | 514/365 |
| 5,405,859 A * | 4/1995 | Ireland | ........................ | 514/365 |
| 5,626,860 A * | 5/1997 | Cincotta et al. | ............. | 424/423 |
| 6,548,485 B2 * | 4/2003 | Khosla et al. | ................. | 514/28 |
| 6,750,247 B2 | 6/2004 | Crews et al. | | |
| 6,787,161 B2 | 9/2004 | Aylward | | |
| 6,960,648 B2 | 11/2005 | Bonny | | |
| 6,982,252 B2 * | 1/2006 | Paglin et al. | .................... | 514/28 |
| 7,151,116 B2 * | 12/2006 | Wender et al. | .............. | 514/450 |
| 2003/0032594 A1 | 2/2003 | Bonny | | |

FOREIGN PATENT DOCUMENTS

WO     WO 01/02413     1/2001

OTHER PUBLICATIONS

Nicolaou et al. Total synthesis of the originally proposed and revised structures of palmerolide A and isomers thereof. J Am Chem Soc. 2008; 130(11):3633-3644.*

Lindsay et al. Structural studies of cytotoxic marine alkaloids: synthesis of novel ring-E analogues of ascididemin and their in vitro and in vivo biological evaluation. Tetrahedron. 2000;56:497-505, abstract only.*

Bax, A., et al. "Improved resolution and sensitivity in $^1$H detected heteronuclear multiple-bond correlation spectroscopy" *J. Mag. Res.*, 1986, pp. 186-191, vol. 78.

Braunschweiler, L. et al. "Coherence transfer by isotropic mixing: application to proton correlation spectroscopy" *J. Mag. Res.*, 1983, pp. 521-528, vol. 53.

De Bruijn, J. et al. "Determination of octanol/water partition coefficients for hydrophobic organic chemicals with the 'slow-stirring' method" *Environ. Toxicol. Chem.*, 1989, pp. 449-512, vol. 8, abstract.

Ellegaard, J. et al. "Elevated lymphocyte ATP-ase activity in patients with cancer of the uterine cervix" *Acta Obstet. Gynecol. Scand.*, 1975, pp. 223-226, vol. 54.

Li, G. et al. "Catalytic aminohydroxylations (AA) of olefins," *Angew Chem. Int. Ed. Engl.*, 1996, pp. 451-454, vol. 35, abstract.

Lipshutz, B.H. et al. "Beta-(trimethylsilyl) ethoxymethyl chloride—a new reagent for the protection of the hydroxyl group" *Tetrahedron Lett.*, 1980, pp. 3343-3346, vol. 21.

Wu, Y. et al. "Revision of the absolute configuration of salicylihalamide A through asymmetric total synthesis" *Angew. Chem. Int. Ed.*, 2000, pp. 4308-4310, vol. 39.

Bax, A. et al. "$^1$H and $^{13}$C Assignments from sensitivity-enhanced detection of heteronuclear multiple-bond connectivity by 2D multiple quantum NMR" *J. Am. Chem. Soc.*, 1986b, pp. 2093-2094, vol. 108, (1986).

Boyd, M.R. et al. "Discovery of a novel antitumor benzolactone enamide class that selectively inhibits mammalian vacuolar-type ($H^+$)-ATPases" *J. Pharmacol. Exp. Ther.* pp. 114-120, vol. 297, No. 1, (2001).

Li, G. et al., "Catalytic aminohydroxylations (AA) of olefins," *Angew Chem. Int. Ed. Engl.*, 1996, pp. 451-454, vol. 35.

Schlosser, M. et al. "Trans-selective olefin synthesis" *Angew. Chem. Int. Ed. Engl.*, 1966, pp. 126, vol. 5.

* cited by examiner

*Primary Examiner*—Yvonne L. Eyler
*Assistant Examiner*—Charlesworth Rae
(74) *Attorney, Agent, or Firm*—Saliwanchik, Lloyd & Saliwanchik

(57) ABSTRACT

A compound or groups of compounds, present in an active principle, derived from tunicates of the species *Synoicum adareanum*, as well as to pharmaceutical compositions comprising these compounds. Extracts from tunicates show selective toxicity against several different cancer cell lines in the NCI 60 cell line panel. These compounds are useful in the effective treatment of cancers, particularly malignant melanomas, colon cancer, and renal cancer cell lines.

19 Claims, 19 Drawing Sheets

Fig.2

| Position | δ¹H (ppm, mult, J (Hz)) | δ¹³C | HMBC |
|---|---|---|---|
| 1 | | 168.1 | |
| 2 | 5.78 (1H, d, 15.2) | 121.3 | 1, 4 |
| 3 | 6.72 (1H, ddd, 5.0, 9.9, 15.2) | 150.0 | 1, 2, 4, 5 |
| 4 | 2.11 (2H, m) | 32.6 | 2, 3, 5, 6 |
| 5 | a 1.30 (1H, m) | 25.7 | 7 |
|   | b 1.05 (1H, m) | | 6 |
| 6 | a 1.50 (1H, ddd, 4.5, 8.2, 11.2) | 38.5 | 5, 7, 8 |
|   | b 1.30 (1H, m) | | 5, 7, 8 |
| 7 | 3.83 (1H, ddd, 4.4, 7.4, 7.6) | 74.5 | 5, 9 |
| 8 | 5.55 (1H, dd, 7.7, 15.5) | 134.3 | 6, 7, 9, 10 |
| 9 | 5.50 (1H, dd, 2.9, 15.5) | 129.6 | 7, 8, 10 |
| 10 | 4.15 (1H, br s) | 69.9 | |
| 11 | 4.49 (1H, dd, 2.2, 5.0, 10.5) | 73.2 | 9, 10, 12/13, CONH₂ |
| 12 | a 1.59 (1H, m) | 30.1 | 12/13 |
|    | b 0.98 (1H, m) | | 11, 12/13 |
| 13 | 1.96 (2H, m) | 30.1 | 12/13, 14, 15 |
| 14 | 5.42 (1H, ddd, 4.7, 10.1, 14.6) | 132.7 | 12/13, 16 |
| 15 | 6.05 (1H, dd, 11.1, 14.6) | 128.4 | 12/13, 16, 17 |
| 16 | 5.60 (1H, d, 11.4) | 127.1 | 14, 15, 18, 25 |
| 17 | | 132.3 | |
| 18 | a 2.17 (1H, dd, 1.3, 13.2) | 43.9 | 16, 17, 19, 25 |
|    | b 2.00 (1H, dd, 11.2, 13.2) | | 16, 17, 19, 20, 25 |
| 19 | 4.85 (1H, ddd, 1.3, 7.4, 11.2) | 75.8 | 1, 17, 18, 20, 21, 26 |
| 20 | 2.69 (1H, qdd, 6.5, 7.4, 9.6) | 37.3 | 18, 19, 21, 22, 26 |
| 21 | 5.14 (1H, d, 9.6) | 136.5 | 19, 20, 23, 26, 27 |
| 22 | | 133.3 | |
| 23 | 5.85 (1H, d, 14.2) | 117.2 | 21, 22, 24, 25 |
| 24 | 6.86 (1H, dd, 10.1, 14.2) | 122.9 | 22, 23, 1' |
| 25 | 1.62 (3H, s) | 13.3 | 21, 22, 23 |
| 26 | 0.90 (3H, d, 6.5) | 17.7 | 19, 20, 21 |
| 27 | 1.71 (3H, s) | 16.9 | 16, 17, 18 |
| 1' | | 163.9 | |
| 2' | 5.70 (1H, br s, 1.0) | 118.8 | 1', 3', 4', 5' |
| 3' | | 152.5 | |
| 4' | 1.83 (3H, s) | 27.7 | 1', 2', 3', 5' |
| 5' | 2.13 (3H, s) | 20.4 | 1', 2', 3', 4' |
| CONH₂ | 6.40 (2H, br) | 157.3 | |
| 24-NH | 9.84 (1H, d, 10.1) | | 23, 24, 1' |
| 10-OH | 5.18 (1H, d, 4.9) | | 9, 10, 11 |
| 7-OH | 4.69 (1H, d, 3.9) | | 6, 7, 8 |

Fig.4

PALMEROLIDE A

| Panel/Cell Line | Percent Growth | | | | |
|---|---|---|---|---|---|
| | -8 | -7 | -6 | -5 | -4 |
| Leukemia | | | | | |
|   CCRF-CEM | 74 | 58 | 62 | 57 | 52 |
|   HL60(TB) | 69 | 76 | 66 | 42 | 17 |
|   K-562 | 70 | 55 | 51 | 21 | 8 |
|   MOLT-4 | 39 | 45 | 36 | 36 | 18 |
|   RPMI-8226 | 44 | 44 | 46 | 32 | 41 |
|   SR | 34 | 30 | 28 | 25 | 24 |
| Non-Small Cell Lung Cancer | | | | | |
|   A549/ATCC | 65 | 54 | 52 | 25 | -83 |
|   EKVX | 127 | 116 | 103 | 58 | -90 |
|   HOP-62 | N/A | N/A | N/A | N/A | N/A |
|   HOP-92 | 78 | 72 | 70 | 66 | -3 |
|   NCI-H226 | N/A | N/A | N/A | N/A | N/A |
|   NCI-H23 | N/A | N/A | N/A | N/A | N/A |
|   NCI-H322M | N/A | N/A | N/A | N/A | N/A |
|   NCI-460 | 82 | 93 | 83 | 13 | -90 |
|   NCI-H522 | 110 | 108 | 88 | 25 | -80 |
| Colon Cancer | | | | | |
|   COLO 205 | 58 | 57 | 61 | 29 | -39 |
|   HCC-2998 | 53 | -4 | -9 | -59 | -99 |
|   HCT-116 | 51 | 45 | 51 | 11 | -100 |
|   HCT-15 | 90 | 88 | 82 | 32 | -69 |
|   HT29 | 94 | 65 | 69 | 12 | -34 |
|   KM12 | 53 | 46 | 45 | 2 | -42 |
|   SW-620 | 70 | 69 | 76 | 35 | -83 |
| CNS Cancer | | | | | |
|   SF-268 | 93 | 93 | 44 | 13 | -82 |
|   SF-295 | 81 | 65 | 41 | -9 | -78 |
|   SF-539 | 100 | 67 | 56 | -61 | -89 |
|   SNB-19 | 123 | 135 | 130 | 85 | -43 |
|   SNB-75 | 40 | 23 | 29 | -13 | |
|   U251 | 83 | 76 | 58 | 34 | -70 |

Fig.5

| | | | | | | |
|---|---|---|---|---|---|---|
| Melanoma | | | | | | |
| | LOX IMVI | 53 | 47 | 37 | 17 | -44 |
| | M14 | -20 | -54 | -65 | -91 | -97 |
| | SK-MEL-2 | 52 | 55 | 55 | -1 | -62 |
| | SK-MEL-28 | 131 | 115 | 108 | 16 | -29 |
| | SK-MEL-5 | 56 | 60 | 42 | 4 | -70 |
| | UACC-257 | 53 | 44 | 29 | -1 | -80 |
| | UACC-62 | 2 | -29 | -11 | -39 | -68 |
| Ovarian Cancer | | | | | | |
| | IGROV1 | 50 | 69 | 50 | 56 | -82 |
| | OVCAR-3 | 72 | 51 | 28 | -4 | -75 |
| | OVCAR-4 | 97 | 88 | 98 | 70 | -21 |
| | OVCAR-5 | 70 | 76 | 65 | 53 | -99 |
| | OVCAR-8 | 105 | 100 | 93 | 26 | -80 |
| | SK-OV-3 | 121 | 110 | 103 | 90 | -59 |
| Renal Cancer | | | | | | |
| | 786-0 | 124 | 113 | 104 | 40 | -88 |
| | A498 | N/A | N/A | N/A | N/A | N/A |
| | ACHN | 107 | 114 | 72 | 42 | -56 |
| | CAKI-1 | 91 | 83 | 44 | 20 | -87 |
| | RFX 393 | | -8 | -21 | -57 | -85 |
| | SN12C | 100 | 93 | 93 | 67 | -51 |
| | TK-10 | 82 | 76 | 56 | -30 | -76 |
| | UO-31 | 93 | 86 | 57 | 21 | -95 |
| Prostate Cancer | | | | | | |
| | PC-3 | 76 | 79 | 72 | 48 | 1 |
| | DU-145 | N/A | N/A | N/A | N/A | N/A |
| Breast Cancer | | | | | | |
| | MCF7 | -17 | 24 | -18 | -78 | -99 |
| | NCI/ADR-RES | 100 | 99 | 85 | 39 | -84 |
| | MDA-MB-231/ATCC | 95 | 79 | 75 | 23 | -72 |
| | HS 578T | N/A | N/A | N/A | N/A | N/A |
| | MDA-MB-435 | 90 | 84 | 62 | 31 | -80 |
| | BT-549 | 67 | 53 | 56 | 11 | -78 |
| | T-47D | 140 | 85 | 139 | 99 | 36 |

Fig.11

Palmerolide C NMR Data

| Position | ¹H (ppm, mult, J (Hz)) | ¹³C | gHMBC |
|---|---|---|---|
| 1 | | 165.32 | |
| 2 | 5.73 (1H, d, 15.5) | 121.33 | 1, 4 |
| 3 | 6.77 (1H, dt, 7.5, 15.5) | 148.92 | 1, 4, 5 |
| 4 | 1.35 (1H, m) | 31.02 | 3, 5, 6 |
| | 2.13 (1H, m) | 31.02 | 2 |
| 5 | 1.89 (1H, m) | 31.42 | 6, 7 |
| | 1.98 (1H, m) | 31.42 | 7 |
| 6 | 5.54 (1H, m) | 131.22 | 5, 7, 8 |
| 7 | 5.58 (1H, m) | 130.4 | 8 |
| 8 | 3.96 (1H, dd, 1.8, 5.6) | 72.2 | 6, 7 |
| 9 | 3.56 (1H, dd, 1.0, 6.6) | 75.00 | 8, 10 |
| 10 | 4.56 (1H, ddd, 2.2, 6.9, 10.7) | 73.76 | 8, OCONH₂ |
| 11 | 1.30 (1H, m) | 27.94 | 10 |
| | 1.49 (1H, m) | 27.94 | |
| 12 | 1.95 (1H, m) | 30.27 | 10 |
| | 1.54 (1H, m) | 30.27 | 13, 14 |
| 13 | 1.90 (1H, m) | 29.48 | 15 |
| | 1.99 (1H, m) | 29.48 | 14, 15 |
| 14 | 5.46 (1H, ddd, 4.7, 10.0, 14.8) | 131.85 | 13, 15, 16 |
| 15 | 6.08 (1H, dd, 11.2, 14.5) | 126.52 | 13, 14, 16 |
| 16 | 5.63 (1H, d, 11.0) | 128.21 | 14, 15, 27 |
| 17 | | 131.56 | |
| 18 | 2.07 (1H, m) | 43.16 | 16, 17, 19, 27 |
| | 2.18 (1H, m) | 43.16 | 16, 17, 27 |
| 19 | 4.85 (1H, ddd, 2.0, 8.0, 11.2) | 74.07 | 1, 26 |
| 20 | 2.72 (1H, qdd, 7.0, 8.0, 10.0) | 36.81 | 19, 21, 22, 26 |
| 21 | 5.15 (1H, d, 9.5 10.2) | 129.84 | 19, 20, 23, 26, 25 |
| 22 | | 132.70 | |
| 23 | 5.85 (1H, d, 14.5) | 116.55 | 21, 22, 24, 25 |
| 24 | 6.85 (1H, dd, 10.3, 13.8) | 122.17 | 22, 23, 1' |
| 25 | 1.69 (3H, s) | 12.77 | 21, 22, 23 |
| 26 | 0.90 (3H, d, 7.2) | 17.30 | 19, 20, 21 |
| 27 | 1.59 (3H, s) | 15.98 | 16, 17, 18 |
| 1' | | 163.16 | |
| 2' | 5.68 (1H, br t, 1.8) | 118.08 | 1', 4', 5' |
| 3' | | 151.63 | |
| 4' | 1.82 (3H, s) | 27.15 | 2', 3', 5' |
| 5' | 2.11 (3H, s) | 19.72 | 1', 2', 3', 4' |
| OCONH₂ | | 156.91 | |
| OCONH₂ | 6.37 (2H, br) | | |
| 24-NH | 9.85 (1H, d, 11.5) | | 23, 1' |
| 8-OH | 4.62 (1H, d, 5.0) | | 7, 8, 9 |
| 9-OH | 4.72 (1H, d, 5.0) | | 8, 9, 10 |

Fig. 12

PALMEROLIDE C

| Panel/Cell Line | Percent Growth | | | | |
|---|---|---|---|---|---|
| | -8 | -7 | -6 | -5 | -4 |
| Leukemia | | | | | |
| CCRF-CEM | 98 | 86 | 60 | -24 | -24 |
| HL60(TB0 | 101 | 92 | 64 | 1 | -23 |
| K-562 | 84 | 63 | 55 | 18 | 16 |
| MOLT-4 | 84 | 44 | 16 | -60 | -78 |
| RPMI-8226 | 68 | 45 | 6 | -32 | -29 |
| SR | | | | | |
| Non-Small Cell Lung Cancer | | | | | |
| A549/ATCC | 86 | 71 | 45 | 19 | -11 |
| EKVX | 102 | 107 | 118 | 86 | -56 |
| HOP-62 | 102 | 105 | 99 | -17 | -74 |
| HOP-92 | 100 | 88 | 54 | 10 | -67 |
| NCI-H226 | 104 | 102 | 115 | 89 | -43 |
| NCI-H23 | 99 | 88 | 70 | -13 | -82 |
| NCI-H322M | 103 | 102 | 111 | 55 | -60 |
| NCI-460 | 95 | 83 | 86 | 21 | |
| NCI-H522 | 97 | 95 | 87 | 14 | -33 |
| Colon Cancer | | | | | |
| COLO 205 | 97 | 90 | 76 | 9 | 2 |
| HCC-2998 | 109 | 83 | 92 | -75 | -77 |
| HCT-116 | 92 | 59 | 56 | -25 | -85 |
| HCT-15 | 91 | 87 | 79 | -51 | -60 |
| HT29 | 85 | 73 | 53 | -3 | 3 |
| KM12 | 100 | 100 | 95 | 21 | -20 |
| SW-620 | 95 | 95 | 91 | 14 | -3 |
| CNS Cancer | | | | | |
| SF-268 | 101 | 107 | 106 | 59 | -46 |
| SF-295 | 87 | 55 | -26 | -66 | -89 |
| SF-539 | 99 | 103 | 113 | 12 | -71 |
| SNB-19 | 92 | 115 | 105 | 57 | -13 |
| SNB-75 | 66 | 56 | 19 | 16 | -37 |
| U251 | 103 | 99 | 68 | 21 | -89 |

Fig.13

Melanoma

| | | | | | |
|---|---|---|---|---|---|
| LOX IMVI | 106 | 103 | 78 | -10 | -4 |
| M14 | 95 | 55 | -41 | -80 | -85 |
| SK-MEL-2 | 107 | 96 | 79 | 7 | -46 |
| SK-MEL-28 | 93 | 96 | 85 | 20 | -23 |
| SK-MEL-5 | 104 | 82 | 55 | -55 | -48 |
| UACC-257 | 85 | 72 | 41 | -22 | -52 |
| UACC-62 | 98 | 99 | 24 | -43 | -56 |

Ovarian Cancer

| | | | | | |
|---|---|---|---|---|---|
| IGROV1 | 88 | 61 | 77 | 37 | -42 |
| OVCAR-3 | 104 | 95 | 85 | -66 | -91 |
| OVCAR-4 | 88 | 98 | 104 | 32 | -49 |
| OVCAR-5 | 120 | 129 | 124 | 72 | -72 |
| OVCAR-8 | 97 | 97 | 94 | 29 | -12 |
| SK-OV-3 | 98 | 108 | 109 | 73 | -9 |

Renal Cancer

| | | | | | |
|---|---|---|---|---|---|
| 786-0 | 96 | 91 | 82 | -10 | -88 |
| A498 | 101 | 106 | 81 | -5 | -50 |
| CAKI-1 | 74 | 41 | -19 | -56 | -93 |
| RFX 393 | 72 | 62 | 55 | -14 | -40 |
| SN12C | 96 | 94 | 87 | 46 | -33 |
| TK-10 | 101 | 101 | 171 | 64 | -55 |
| UO-31 | 99 | 100 | 63 | -27 | -47 |

Prostate Cancer

| | | | | | |
|---|---|---|---|---|---|
| PC-3 | 95 | 88 | 64 | -14 | -88 |
| DU-145 | 96 | 101 | 90 | 52 | -88 |

Breast Cancer

| | | | | | |
|---|---|---|---|---|---|
| MCF7 | 100 | 94 | 47 | 9 | -40 |
| NCI/ADR-RES | 106 | 107 | 109 | 54 | -56 |
| MDA-MB-231/ATCC | 100 | 106 | 72 | -15 | -40 |
| HS 578T | 92 | 91 | 81 | 31 | -9 |
| MDA-MB-435 | 98 | 76 | 67 | -65 | -81 |
| BT-549 | 95 | 104 | 97 | 52 | -43 |
| T-47D | 96 | 92 | 60 | 50 | 12 |

Fig.16

Palmerolide D NMR Data

| Position | $^1$H (ppm, mult, J (Hz)) | $^{13}$C | gHMBC |
|---|---|---|---|
| 1 | | 166.08 | |
| 2 | 5.76 (1H, d, 15.8) | 121.18 | 1, 3, 4 |
| 3 | 6.71 (1H, ddd) | 150.02 | 1, 2, 4 |
| 4 | 2.11 (1H, m) | 33.04 | 2, 3, 5 |
|  | 2.15 (1H, m) | 33.04 | 2, 3 |
| 5 | 1.98 (1H, m) | 50.08 | 3, 4 |
|  | 1.30 (1H, m) | 58.35 | 3, 6 |
| 6 | 1.48 (1H, m) | 38.35 | |
| 7 | 3.82 (1H, m) | 73.17 | 6, 8, 9 |
| 8 | 5.53 (1H, m) | 134.21 | 7, 9, 10 |
| 9 | 5.49 (1H, m) | 129.56 | 7, 8, 11, 12 |
| 10 | 4.15 (1H, m) | 69.92 | 8, 9, 12 |
| 11 | 4.48 (1H, m) | 75.82 | 9, 10, 13 OCONH$_2$ |
| 12 | 1.94 (1H, m) | 30.04 | |
| 13 | 1.94 (1H, m) | 30.04 | |
| 14 | 5.41 (1H, m) | 133.62 | 13, 15, 16 |
| 15 | 6.04 (1H, dd, 11.6, 14) | 126.85 | 14, 16 |
| 16 | 5.59 (1H, d, 12) | 128.37 | 14, 15, 25 |
| 17 | | 132.24 | 15, 16, 18, 25 |
| 18 | 2.16 (1H, m) | 43.87 | 16, 19, 25 |
|  | 2.00 (1H, m) | 43.87 | 16, 19 |
| 19 | 4.04 (1H, m) | 74.50 | 17, 18, 20, 26 |
| 20 | 2.68 (1H, m) | 37.28 | 18, 19, 21, 26 |
| 21 | 5.14 (1H, d, 9.7) | 130.67 | 19, 20, 26, 27 |
| 22 | | 133.34 | 21, 23, 27 |
| 23 | 5.86 (1H, d, 14.6) | 117.47 | 21, 24, 27 |
| 24 | 6.85 (1H, dd, 10.4, 15) | 122.65 | 22, 23, 1' |
| 25 | 1.60 (3H, s) | 16.84 | 15, 16, 18 |
| 26 | 0.89 (3H, d) | 17.74 | 19, 20, 21 |
| 27 | 1.70 (3H, s) | 13.34 | 21, 23 |
| 1' | | 163.49 | |
| 2' | 5.81 (1H, s) | 120.27 | 1', 4', 7' |
| 3' | | 153.23 | |
| 4' | | 40.83 | 2', 3', 5', 7' |
| 5' | | 143.61 | |
| 6' | 4.72 (2H, d) | 112.57 | 4', 8' |
| 7' | 1.76 (3H, s) | 24.76 | 2', 3', 4' |
| 8' | 1.61 (3H, s) | 22.68 | 4', 5', 6' |
| OCONH$_2$ | 6.45 (2H, br) | 157.41 | |
| 24-NH | 9.94 (1H, d, 10.3) | | |

Palmerolide E NMR Data

| Position | $^1$H (ppm, mult, J (Hz)) | $^{13}$C | gHMBC |
|---|---|---|---|
| 1 | | 165.31 | |
| 2 | 5.78 (1H, d, 15.7) | 120.32 | 1, 4 |
| 3 | 6.74 (1H, ddd) | 149.74 | 1, 4, 5 |
| 4 | 2.11 (1H, m) | 32.37 | 2, 3, 5 |
|   | 2.14 (1H, m) | 32.37 | 2, 3 |
| 5 | 1.30 (1H, m) | 24.94 | 7 |
|   | 1.05 (1H, m) | 24.94 | |
| 6 | 1.49 (1H, m) | 34.72 | 4, 5, 7 |
|   | 1.29 (1H, m) | 34.72 | 5, 7 |
| 7 | 3.81 (1H, m) | 72.55 | 5, 9 |
| 8 | 5.53 (1H, dd, 1.4, 8.1) | 133.56 | 7, 9, 10 |
| 9 | 5.49 (1H, d, 2.9) | 128.91 | 7, 8, 10 |
| 10 | 4.12 (1H, m) | 69.22 | 8, 9, 11, 12/13 |
| 11 | 4.47 (1H, ddd, 1.5, 5.1, 10.7) | 75.13 | 9, 10, 12/13, $\underline{C}$ONH2 |
| 12 | 1.05 (2H, m) | 29.39 | 10, 13 |
| 13 | 1.95 (2H, m) | 29.39 | 12 |
| 14 | 5.42 (1H, ddd, 5.0, 10.0, 14.7) | 132.18 | 12/13, 15, 16 |
| 15 | 6.05 (1H, dd, 10.8, 14.8) | 126.30 | 12/13, 17, 16 |
| 16 | 5.61 (1H, d, 10.6) | 127.97 | 15, 14, 18, 27 |
| 17 | | 131.24 | |
| 18 | 2.09 (1H, m) | 42.94 | 16, 19, 20, 27 |
|   | 2.16 (1H, m) | 42.94 | 16, 17, 19, 27 |
| 19 | 5.02 (1H, ddd, 2.2, 7.6, 10.8) | 72.49 | 1, 17, 20, 21, 26 |
| 20 | 2.94 (1H, qdd, 7.0, 7.6, 10.2) | 37.43 | 18, 19, 21, 22, 26 |
| 21 | 6.55 (1H, dd, 1.5, 10.2) | 154.88 | 19, 22, 23, 25, 26 |
| 22 | | 138.88 | |
| 23 | 9.41 (1H, s) | 195.64 | 21, 22, 26 |
| 25 | 1.67 (3H, d, 1.2) | 9.18 | 21, 22, 23 |
| 26 | 1.01 (3H, d, 7.3) | 15.49 | 19, 21, 20 |
| 27 | 1.63 (3H, s) | 16.13 | 16, 17, 18 |
| O$\underline{C}$ONH$_2$ | | 156.66 | |
| OCONH$_2$ | 6.46 (2H, br) | | |

Fig.19

PALMEROLIDE E

| Panel/Cell Line | Percent Growth | | | | |
|---|---|---|---|---|---|
| | -8 | -7 | -6 | -5 | -4 |
| Leukemia | | | | | |
| CCRF-CEM | N/A | N/A | N/A | N/A | N/A |
| HL60(TB0 | 75 | 97 | 94 | 73 | 40 |
| K-562 | 65 | 61 | 55 | 22 | 51 |
| MOLT-4 | 79 | 85 | 92 | 65 | 27 |
| RPMI-8226 | N/A | N/A | N/A | N/A | N/A |
| SR | 101 | 66 | 31 | 9 | 3 |
| Non-Small Cell Lung Cancer | | | | | |
| A549/ATCC | 41 | 44 | 40 | 19 | -44 |
| EKVX | 98 | 102 | 103 | 97 | -40 |
| HOP-62 | 93 | 93 | 90 | -53 | -78 |
| HOP-92 | N/A | N/A | N/A | N/A | N/A |
| NCI-H226 | 107 | 125 | 131 | 105 | -27 |
| NCI-H23 | 75 | 85 | 77 | -30 | -84 |
| NCI-H322M | 93 | 97 | 90 | 70 | -58 |
| NCI-460 | 99 | 92 | 91 | 47 | 1 |
| NCI-H522 | 92 | 80 | 69 | -28 | -29 |
| Colon Cancer | | | | | |
| COLO 205 | 63 | 62 | 36 | 1 | 6 |
| HCC-2998 | 71 | 75 | 62 | -65 | -74 |
| HCT-116 | 57 | 50 | 46 | -66 | -94 |
| HCT-15 | 89 | 86 | 75 | 3 | -93 |
| HT29 | 47 | 53 | 37 | 3 | 4 |
| KM12 | 99 | 98 | 97 | 55 | -32 |
| SW-620 | 77 | 81 | 82 | 6 | 2 |
| CNS Cancer | | | | | |
| SF-268 | 101 | 99 | 101 | 71 | -36 |
| SF-295 | 32 | 20 | -5 | -57 | -62 |
| SF-539 | 100 | 106 | 105 | 40 | -66 |
| SNB-19 | 104 | 107 | 100 | 16 | -8 |
| SNB-75 | 22 | 35 | 25 | 6 | -28 |
| U251 | 107 | 103 | 101 | 43 | -96 |

Fig.20

| | | | | | | |
|---|---|---|---|---|---|---|
| Melanoma | | | | | | |
| | LOX IMVI | 109 | 106 | 110 | 22 | -62 |
| | M14 | -24 | -29 | -57 | -80 | -82 |
| | SK-MEL-2 | 57 | 31 | 12 | -41 | -51 |
| | SK-MEL-28 | 93 | 96 | 79 | -21 | -28 |
| | SK-MEL-5 | 50 | 46 | 50 | -47 | -21 |
| | UACC-257 | 42 | 41 | 28 | -41 | -55 |
| | UACC-62 | 102 | -4 | -22 | -30 | -42 |
| Ovarian Cancer | | | | | | |
| | IGROV1 | 75 | 44 | 46 | 11 | -59 |
| | OVCAR-3 | 77 | 65 | 70 | -51 | -49 |
| | OVCAR-4 | 117 | 122 | 110 | 58 | -20 |
| | OVCAR-5 | 122 | 133 | 125 | 70 | -86 |
| | OVCAR-8 | 101 | 106 | 94 | 21 | -16 |
| | SK-OV-3 | 104 | 107 | 104 | 54 | -22 |
| Renal Cancer | | | | | | |
| | 786-0 | 94 | 91 | 77 | -28 | -37 |
| | A498 | 93 | 93 | 54 | -30 | -35 |
| | ACHN | 102 | 106 | 94 | 34 | -100 |
| | CAKI-1 | | 7 | -18 | -39 | -76 |
| | RFX 393 | 66 | 63 | 61 | -9 | -12 |
| | SN12C | 97 | 95 | 91 | 56 | -1 |
| | TK-10 | 96 | 93 | 91 | 102 | -55 |
| | UO-31 | 105 | 73 | 58 | -35 | -60 |
| Prostate Cancer | | | | | | |
| | PC-3 | N/A | N/A | N/A | N/A | N/A |
| | DU-145 | 95 | 105 | 102 | 58 | -48 |
| Breast Cancer | | | | | | |
| | MCF7 | 102 | 93 | 99 | 14 | -35 |
| | NCI/ADR-RES | 115 | 122 | 110 | 76 | -61 |
| | MDA-MB-231/ATCC | 103 | 82 | 75 | 9 | -18 |
| | HS 578T | 83 | 92 | 87 | 18 | -11 |
| | MDA-MB-435 | 75 | 74 | 56 | -29 | -51 |
| | BT-549 | 95 | 105 | 100 | 56 | -32 |
| | T-47D | 65 | 74 | 60 | 32 | 8 |

CYTOTOXIN COMPOUND AND METHOD OF ISOLATION

CROSS REFERENCE TO RELATED APPLICATIONS

This application claims priority to U.S. Provisional Patent Application No. 60/521,073, having the same title and inventorship, filed Feb. 17, 2004, which is incorporated herein by reference.

GOVERNMENT SUPPORT

This invention was developed under support from the National Science Foundation under grants OPP-9901076 and OPP-0125152; accordingly the U.S. government has certain rights in the invention.

BACKGROUND OF THE INVENTION

One of the greatest efforts of modern medicine is the control and abatement of cellular proliferative disorders, such as cancers. Considerable research has been conducted searching for new biologically active compounds having useful activity for specific cancers and the organisms which produce these compounds. For example, certain marine soft corals have shown to be a source of biologically active cytotoxins. Also, compounds from sponges have proven effective against lipoxygenase-mediated conditions in humans (See U.S. Pat. No. 6,750,247 to Crews et al.)

Tunicates have proven to be an important source of bioactive natural products. Among marine natural products that have advanced as cancer treatments the ecteinascidins and didemnins are derived from tunicates, and the eudistomins have potent antiviral activity. As part of an ongoing study of bioactivity among Antarctic marine invertebrates, the inventors had the occasion to study the tunicate *Synoicum adareanum*.

*S. adareanum* is a circumpolar tunicate common in the shallow waters around Anvers island (64° 46'S, 64° 03'W) on the Antarctic Peninsula from 15 to 796 meters depth. *S. adareanum* colonies consist of large rounded or club-shaped heads with the bottom stalk being wrinkled and leathery and only slightly narrower than the head. *S. adareanum* colonies can be up to eighteen centimeters high with a diameter of twelve centimeters. *S. adareanum* colonies may comprise a single head or, up to six heads can arise from a single stalk.

SUMMARY OF INVENTION

Extracts from *S. adareanum*, Palmerolide A (1), Palmerolide C, Palmerolide D, and Palmerolide E displayed bioactivity in field-based feeding-deterrent assays, leading the inventors to investigate the chemical nature of the activity. Presented are novel, isolated polyketides, Palmerolide A (1), Palmerolide C, Palmerolide D, and Palmerolide E as the major natural product from extracts of *S. adareanum*. These polyketides display selective cytotoxicity in the National Cancer Institute (NCI) 60 cell line panel inhibiting, inter alia, melanoma (UACC-64, LC50 0.018 µM) with three orders of magnitude greater sensitivity relative to other cell lines tested.

In a general embodiment, the present invention provides a method of treating a subject with cancer, comprising administering to the subject a therapeutically effective amount of at least one isolated compound obtained from extracts of a *Synoicum* species. In this embodiment, the *Synoicum* species is *S. adareanum* and the isolated compound obtained from the *Synoicum* species is a Palmerolide. The Palmerolide is chosen from the group consisting of Palmerolide A(1), Palmerolide C, Palmerolide D, and Palmerolide E.

In an alternate embodiment, a composition (or an isomer, racemate or racemic mixture thereof, or a pharmaceutically acceptable salt thereof) is provided comprising an isolated compound of the formula:

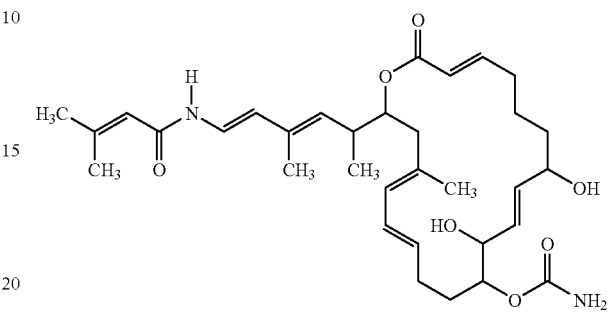

In yet another embodiment the present invention provides for a composition (or an isomer, racemate or racemic mixture thereof, or a pharmaceutically acceptable salt thereof) comprising an isolated compound of the formula:

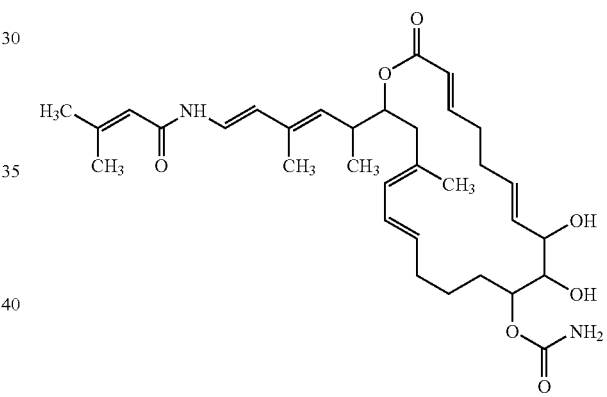

An additional embodiment the present invention provides for a composition (or an isomer, racemate or racemic mixture thereof, or a pharmaceutically acceptable salt thereof) comprising an isolated compound of the formula:

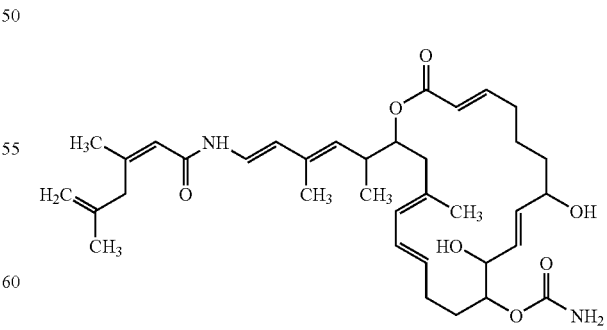

The present invention also provides for a composition (or an isomer, racemate or racemic mixture thereof, or a pharmaceutically acceptable salt thereof) comprising an isolated compound of the formula:

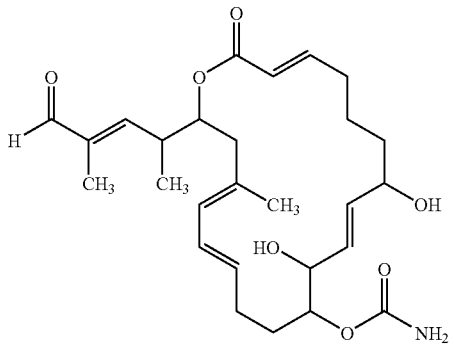

FIG. 18 is a chart showing the NMR Data for Palmerolide E.

FIG. 19 is a chart showing the National Cancer Institute (NCI) Developmental Therapeutics Program In-Vitro Testing Results for Palmerolide E.

FIG. 20 is a continued chart, showing the National Cancer Institute (NCI) Developmental Therapeutics Program In-Vitro Testing Results for Palmerolide E.

FIG. 21 is a graph showing National Cancer Institute (NCI) Developmental Therapeutics Program Dose Response Curves for all cell lines tested for Palmerolide E.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Terms

Those skilled in the art will recognize that the Palmerolide compounds disclosed herein can exist in several tautomeric forms. All such tautomeric forms are considered as part of this invention.

"Pharmaceutically acceptable carrier" refers to any carrier, diluent, excipient, wetting agent, buffering agent, suspending agent, lubricating agent, adjuvant, vehicle, delivery system, emulsifier, disintegrant, absorbent, preservative, surfactant, colorant, flavorant, or sweetener, preferably non-toxic, that would be suitable for use in a pharmaceutical composition.

"Pharmaceutically acceptable equivalent" includes, without limitation, pharmaceutically acceptable salts, hydrates, metabolites, prodrugs and isosteres. Many pharmaceutically acceptable equivalents are expected to have the same or similar in vitro or in vivo activity as the compounds of the invention.

"Pharmaceutically acceptable salt" refers to a salt of the inventive compounds which possesses the desired pharmacological activity and which is neither biologically nor otherwise undesirable. The salt can be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Prodrug" refers to a derivative of the inventive compounds that undergoes biotransformation, such as by metabolism, before exhibiting a pharmacological effect. The prodrug

BRIEF DESCRIPTION OF THE DRAWINGS

For a fuller understanding of the nature and objects of the invention, reference should be made to the following detailed description, taken in connection with the accompanying drawings, in which:

FIG. 2 is a chart showing the NMR Data for Palmerolide A.

FIG. 4 is a chart showing the National Cancer Institute (NCI) Developmental Therapeutics Program In-Vitro Testing Results for Palmerolide A.

FIG. 5 is a continued chart, showing the National Cancer Institute (NCI) Developmental Therapeutics Program In-Vitro Testing Results for Palmerolide A.

FIG. 11 is a chart showing the NMR Data for Palmerolide C.

FIG. 12 is a chart showing the National Cancer Institute (NCI) Developmental Therapeutics Program In-Vitro Testing Results for Palmerolide C.

FIG. 13 is a continued chart, showing the National Cancer Institute (NCI) Developmental Therapeutics Program In-Vitro Testing Results for Palmerolide C.

FIG. 16 is a chart showing the NMR Data for Palmerolide D.

Figure 1:
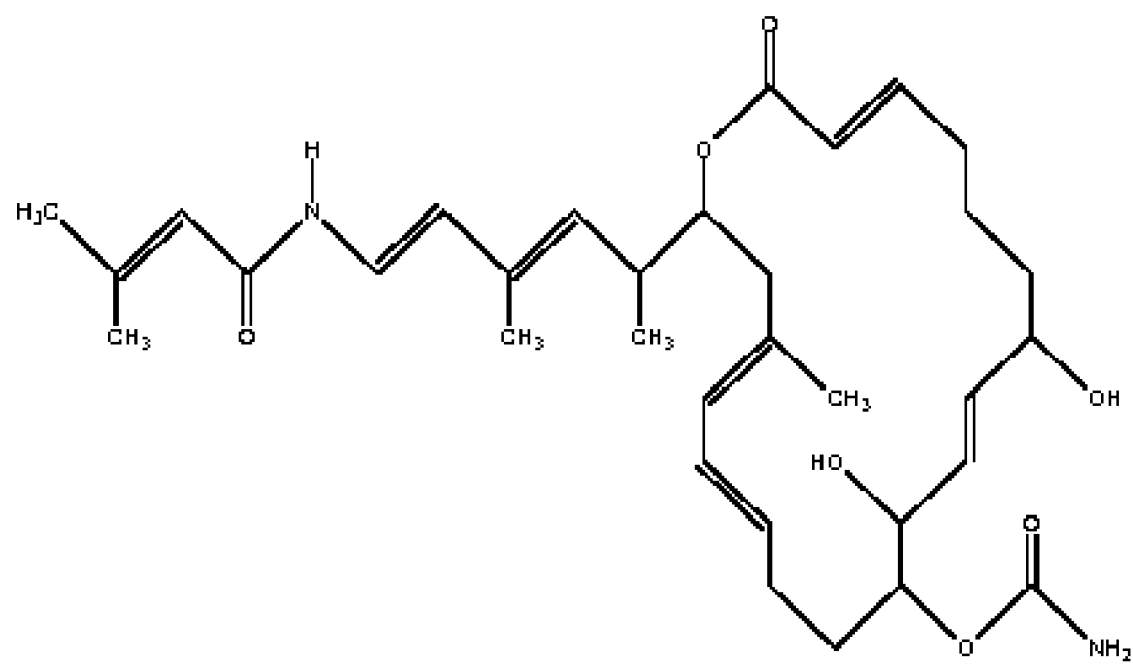
FIG. 1 is a perspective view of the chemical formula for Palmerolide A.

is formulated with the objective of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burger's Medicinal Chemistry and Drug Chemistry, Fifth Ed., Vol. 1, pp. 172-178, 949-982 (1995).

"Palmerolide," as used herein, refers to a multi-membered macrocyclic polyketide bearing carbonate and amide functionality. In one embodiment, the Palmerolide is isolated from the tunicate *Synoicum adareanum*; collected from the vicinity of Palmer Station on the Antarctic Peninsula.

"Polyketides," as used herein, refers to any natural compound containing alternating carbony and methylene groups (β-polyketones), derived from repeated condensation of acetyl coenzyme A.

"Macrocycle," as use herein, refers to a large molecule arranged in a circle with various semi-compounds attached at various points. The point of attachment and the nature of the sub-molecule determines the nature and physiological effect of the compound which contains it.

"Macrolide," as used herein, refers to a class of antibiotics characterized by molecules made up of large-ring lactones.

"Olefin," as used herein, is synonymous with "alkene" and refers to an acyclic hydrocarbon containing one or more double bonds.

As used herein, "a clinical response" is the response of a cell proliferative disorder, such as melanoma, colon and renal cancer, to treatment with novel compounds disclosed herein. Criteria for determining a response to therapy are widely accepted and enable comparisons of the efficacy alternative treatments (see Slapak and Kufe, Principles of Cancer Therapy, in Harrisons's Principles of Internal Medicine, 13th edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or tumor or the appearance of new lesions or tumors. The response to treatment is evaluated after the subjects had completed therapy.

Pharmaceutical Compositions

A "pharmaceutical composition" of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

A "therapeutically effective amount" is the amount of Palmerolide A, C, D, or E, or any combination thereof necessary to provide a therapeutically effective amount of the corresponding compound in vivo. The amount of the compound must be effective to achieve a response, including but not limited to total prevention of (e.g., protection against) and to improved survival rate or more rapid recovery, or improvement or elimination of symptoms associated with a cellular proliferative disease or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

Example I

Hollow Fiber Assay for Preliminary In Vivo Testing

The Biological Testing Branch of the Developmental Therapeutics Program has adopted a preliminary in vivo screening tool for assessing the potential anticancer activity of compounds identified by the large scale in vitro cell screen. This hollow fiber based assay has been in use since June, 1995.

Each compound is tested against a standard panel of 12 human tumor cell lines including NCI-H23, NCI-H522, MDA-MB-231, MDA-MB-435, SW-620 COLO 205, LOX IMVI, UACC-62, OVCAR-3, OVCAR 5, U251 and SF-295. The cell lines are cultivated in RPMI-1640 containing 10% FBS and 2 mM glutamine. On the day preceding hollow fiber preparation the cells are given a supplementation of fresh medium to maintain log phase growth. For fiber preparation the cells are harvested by standard trypsinization technique and resuspended at the desired cell density (varies by cell line between 2-10×106 cells/ml). The cell suspension is flushed into 1 mm I.D. polyvinylidene hollow fibers with a molecular weight exclusion of 500,000 Da. The hollow fibers are heat-sealed at 2 cm intervals and the samples generated from these seals are placed into tissue culture medium and incubated at 37° C. in 5% CO2 for 24-48 hours prior to implantation. A total of 3 different tumor lines are prepared for each experiment so that each mouse receives 3 intraperitoneal implants (1 of each tumor line) and 3 subcutaneous implants (1 of each tumor line). On the day of implantation, samples of each tumor cell line are quantitated for viable cell mass by a stable endpoint MTT assay so that the time zero (0) cell mass is known. Thus, the cytostatic and cytocidal capacities of the test compound can be assessed. Mice are treated with experimental agents starting on day 3 or 4 following fiber implantation and continuing once daily for a total of 4 doses. Each agent is assessed by intraperitoneal injection at 2 dose levels with 3 mice/dose/experiment. Vehicle controls consist of 6 mice receiving the compound diluent only. The fibers are collected from the mice on the day following the fourth compound treatment and subjected to the stable endpoint MTT assay. The optical density of each sample is determined spectrophotometrically at 540 nm and the mean of each treatment group is calculated. The percent net cell growth in each treatment group is calculated and compared to the percent net cell growth in the vehicle treated controls. Each compound is assessed in a total of 4 experiments (3 cell lines/experiment×4 experiments=12 cell lines).

Compounds are selected for further testing (e.g. time/dose exposure studies preliminary pharmacology studies, subcutaneous xenograft efficacy studies) on the basis of several hollow fiber assay criteria. These include: (1) a reduction in net cell growth of 50% or greater in 10 of the 48 possible test combinations (12 cell lines×2 sites×2 compound doses); (2) a reduction in net cell growth of 50% or greater in a minimum of 4 of the 24 distant site combinations (intraperitoneal drug/subcutaneous culture); and/or (3) cell kill of 1 or more cell lines in either implant site (reduction in the viable cell mass below the level present at the start of the experiment).

To simplify evaluation, a point system has been adopted which allows rapid viewing of the activity of a given compound. For this, a value of 2 is assigned for each compound dose which results in a 50% or greater reduction in viable cell mass. The intraperitoneal and subcutaneous samples are scored separately so that criteria (1) and (2) can be evaluated. Compounds with a combined IP+SC score 20, a SC score 8 or a net cell kill of one or more cell lines can be considered for further studies. The maximum possible score for an agent is 96 (12 cell lines×2 sites×2 dose levels×2 [score]). These criteria were statistically validated by comparing the activity outcomes of >80 randomly selected compounds in the hollow fiber assay and in xenograft testing. This comparison indicated that there was a very low probability of missing a xenograft active compound if the hollow fiber assay were used as the initial in viva screening tool. Because of the design of the hollow fiber assay, the results of individual cell lines are not reported since the statistical power of the assay is based on the impact of a compound against the entire panel of cells. In addition to the hollow fiber results, other factors (e.g. unique structure, mechanism of action, etc.) may result in referral of a compound for further studies without the corn pound meeting these hollow fiber assay criteria.

Example II

Palmerolide Isolation

*S. adareanum* was extracted with 1:1 dichloromethane/methanol and the residue resulting from rotary evaporation was partitioned between an equal volume of water and ethyl acetate (EtOAc). Column chromatography of the EtOAc partition fraction using mixtures of hexane, ethyl acetate and methanol resulted in Fractions 4 and 5, which eluted with 2%-5% methanol/ethyl acetate (310 mg) combined. These combined fractions were further separated by gradient elution of 1-10% MeOH/CHCl3 followed up by purification with HPLC on C-18 (40% H2O/MeCN) afforded Palmerolide A, C, D and E (see Table I below).

(H-10). While H-10 showed no gHMBC correlations, H-8, H-9 and H-11 all displayed connectivity by gHMBC to C-10. H-11 could be further extended to C-12/C-13 (C-12 and C-13 are coincident in the 13C NMR spectrum) by gHMBC and gCOSY, as well as to an ester carbonyl (OCOX) which displayed no further connectivity using these NMR techniques. In the gHMBC spectrum, H-13 coupled into the olefinic

TABLE I

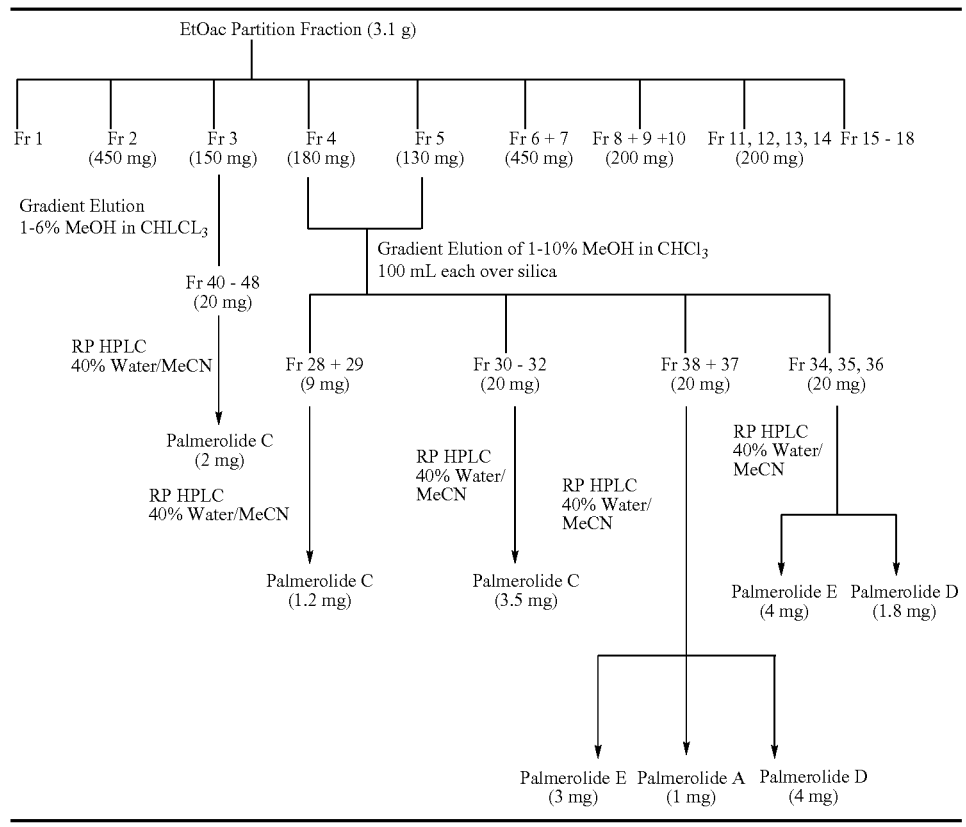

Example III

Palmerolide A(1)

As an illustrative example; Palmerolide A(1) was isolated as a white amorphous solid from the 1:1 methanol/ethyl acetate fraction eluting from silica gel chromatography of the crude (1:1 methanol/dichloromethane) extract. Mass spectrometric analysis provided a molecular formula of $C_{33}H_{48}N_2O_7$ (FIG. 1) (HRFABMS m/z 585.3539, $\Delta 0.1$ mmu for [M++1]). The C-1 to C-24 carbon backbone of Palmerolide A was unambiguously established based on 1H-1H and 1H-13C connectivity assignments from 2D NMR techniques as described below.

Figure 3:
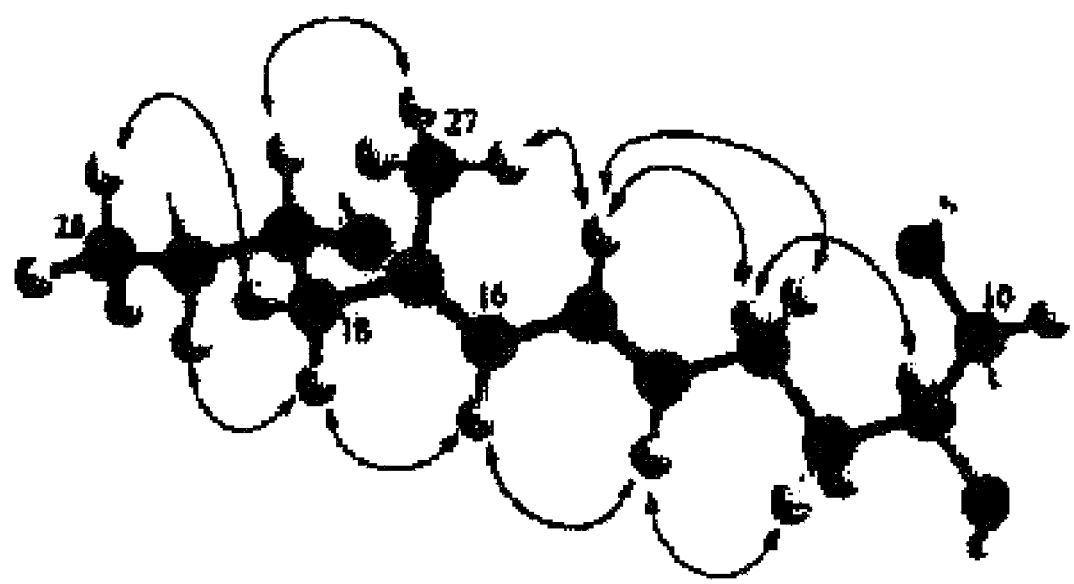
FIG. 3 depicts selected ROE correlations relating the relative stereochemistry between C-11 and C-19.

The C-1 ester carbonyl of Palmerolide A (1) was found to be conjugated to the C-2/C-3 olefin based on observation of cross-correlations in the gHMBC spectrum (FIG. 2) from both H-2 and H-3 to C-1. The olefinic protons were disposed trans based on the large vicinal coupling (J=152 Hz). Three methylene carbons ($\delta 32.6$, 25.7 and 38.5) were observed by both gCOSY and gHMBC to intervene between the C-2/C-3 olefin and a hydroxymethine at $\delta 3.83$ (H-7). A trans-distributed olefin (J=15.5 Hz) could be positioned between the aforementioned hydroxymethine and another at $\delta 4.15$ region, to C-14 and C-15. The C-14/C-15 trans-olefin (J=14.6 Hz) was shown to be conjugated to a tri-substituted olefin in positions C-16 and C-17 by gHMBC correlations of H-14, H-15, H-18 and H-19, as well as H3-27. The C-16/C-17 olefin must be E based on a ROESY spectrum, which demonstrated the proximity (FIG. 3) of H3-27 to H-15. A methylene group (C-18, $\delta 43.9$) intervenes between the C-16/C-17 olefin and an oxygen-bearing methine (C-19, $\delta 75.8$), based on gHMBC correlations of H-16 and H3-27 to C-18; H-19 and H-20 similarly correlate to C-18. The 20-membered macrocycle was completed based on coupling between H-19 and the C-1 ester carbonyl in the gHMBC spectrum.

Features of the macrocycle were established by further analysis of 2D NMR data. In addition to the four E olefins described above, three oxygen atoms and one methyl group were pendant on the macrocycle. Hydroxymethine protons at H-7 and H-10 were conclusively assigned based on observation of coupling of the hydroxyl protons in both the gHMBC and gCOSY spectra: in the gHMBC spectrum, the hydroxyl protons correlated to the respective α- and β-carbons, while in the gCOSY spectrum correlations were observed between the hydroxyl protons and their respective hydroxymethines. The third oxygen-bearing carbon (C-11), as described above, correlates with an ester carbonyl (OCOX) at $\delta 157.3$.

Also pendant on the macrocycle is the C-19 side chain. The H-20 multiplet, correlating to C-19 (gHMBC), was shown by gCOSY to be coupled to a methyl group (C-26, δ0.90) and the terminus of a conjugated diene system based on H-19 and H-20 gHMBC correlations to olefinic C-21 (δ130.5). Both the C21/C-22 and the C-23/C-24 olefins were determined to be E, based, in the former case, on a ROESY correlation between H3-25 and H-20, and in the latter case the basis of coupling (J=14.2 Hz). Connectivity of the C-23/C-24 olefin could be established based on gHMBC correlations of H-23 to C-21, C-22, C-24 and C-25. C-24 marked the terminus of the contiguous carbon chain and could be shown to bear an —NH group due to gHMBC correlations of an amide proton at δ9.84 to carbons C-23, C-24 and the amide carbonyl, C-1' (δ163.9).

The isopentenoyl substructure (C-1' to C-5') was unusual in displaying 4JCH coupling in the gHMBC spectrum between the amide carbonyl (C-1) and both vinyl methyl groups (C-4' and C-5). Only one vinyl methyl can be placed within the 3JCH reach of the typical HMBC experiment optimized for 8 Hz. The 2-methyl- 2-butenoyl isomer, wherein protons from one vinyl methyl reside three bonds from the carbonyl and those from the second reside four bonds distant was unlikely on chemical shift grounds, but also because the vinyl methyl groups were mutually correlated in the gHMBC spectrum, FIG. 2. The substructure was secured as the isopentenoyl group by observation of very small coupling (J=1.0 Hz) of the vinyl proton (H-2') to both vinyl methyl groups (C-4' and C-5), excluding a vicinal relationship (i.e., large J) between the vinyl proton and one vinyl methyl required by the 2-methyl-2-butenoyl isomer.

The connectivity described above established the full planar structure of Palmerolide A (1) with the exception of a single open valence on the ester carbonyl attached to the macrolide at C-11. Remaining to be accounted from the molecular formula was —NH2. That the C-11 functional group was a carbamate is supported by the precedence of that functional group on other polyketides, most notably the anticancer agent discodermolide.

The stereochemical assignment of Palmerolide A's (1) five asymmetric centers was established by the application of the modified Mosher and Murata methods. (R)- and (S)-MTPA esters's of Palmerolide A demonstrated both C-7 and C-10 to bear the R configuration. Configurational analysis of the C-10/C-11 fragment identified a gauche relationship between H-10 and H-11, based on the small 3JH-10/H-11 observed between the vicinal protons and the large 3JCH for both the H-10/C-12 and the H-11/C-9 relationships. Further support for the conformation was found in 2JC-11/H-10 and 2JC-10/h-11, both of which were large and negative, defining the absolute stereochemistry of C-11 as R. Similarly, configurational analysis of the C-19/C-20 system suggested an anti relationship of the respective protons, based on the large 3JH-19/H-20, small 3JC-21/H-19, 3JC-26/H-19 and 3JC-18/H-20, as well as the large 3JC-19/H-20. The relative position of C-18 in this fragment was secured by the observation of ROESY correlations between H2-18 and H-20 as well as H2-18 and H3-26 while no ROESY correlation was observed between H2-18 and H-21, requiring the relative configuration 19R*, 20S*.

The four olefins in the macrocycle constrain the flexibility often found in macrolides, facilitating stereochemical analysis by NOE studies. Further analysis of the ROESY spectrum revealed the macrolide to adopt two largely planar sides of a tear-drop shaped cycle, one side consisting of C-1 through C-6, the other C-11 through C-19, with C-7 through C-10 providing a curvilinear connection. In particular, H-19, H3-27, H-15 and H2-13 (see FIG. 3) are sequentially correlated in the ROESY spectrum, as are H3-26, H2-18, H-16, H-14 and H-12, defining the periphery of the top and bottom face of the western hemisphere. H-11 correlates only to the top series of protons, a result consistent only with C-19 and C-11 both adopting the R configuration. The absolute stereochemistry of the C-19/C-20 fragment is therefore 19R, 20S.

Tunicates are not well known as producers of type I polyketides, though the patellazoles and iejimalides are significant, bioactive, representatives. Palmerolide A (1) is unusual in bearing a small macrocycle, with 20 members, compared to 24 in the patellazoles and iejimalides, and a vinyl amide, a feature more commonly associated with cyanophyte-derived macrolides such as tolytoxin. Palmerolide A displays cytotoxicity toward several other melanoma cell lines, FIG. 2, [M14(LC50 0.076 μM), SK-MEL-5 (6.8 μM) and LOX IMVI (9.8 μM)] as well as the previously mentioned UACC-62. Besides melanoma, FIG. 3, one colon cancer cell line (HCC-2998, 6.5 μM), FIG. 4, and one renal cancer cell line (RXF 393, 6.5 μM), FIG. 5, Palmerolide A was largely devoid of cytotoxicity (LC50>10 μM), representing a selectivity index among tested cell lines of 103 for the most sensitive cells. Significantly, Palmerolide A is COMPARE.-negative against the NCI database, suggestive of a previously un-described mechanism of action. Field and laboratory bioassay and chemical studies to address Palmerolide A's potential are ongoing.

Figure 6:
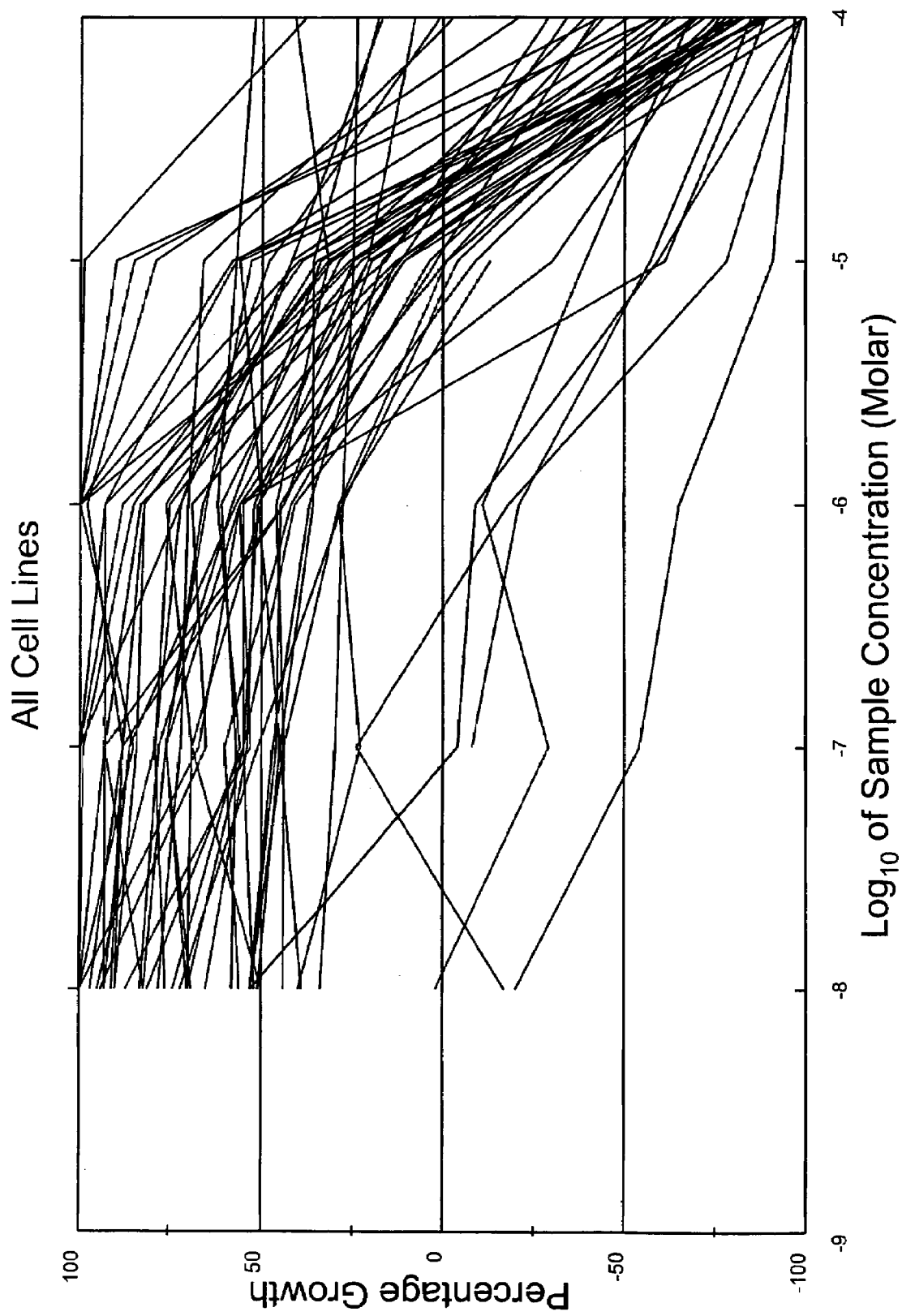
FIG. 6 is a graph showing National Cancer Institute (NCI) Developmental Therapeutics Program Dose Response Curves for all cell lines tested for Palmerolide A.
Figure 7:
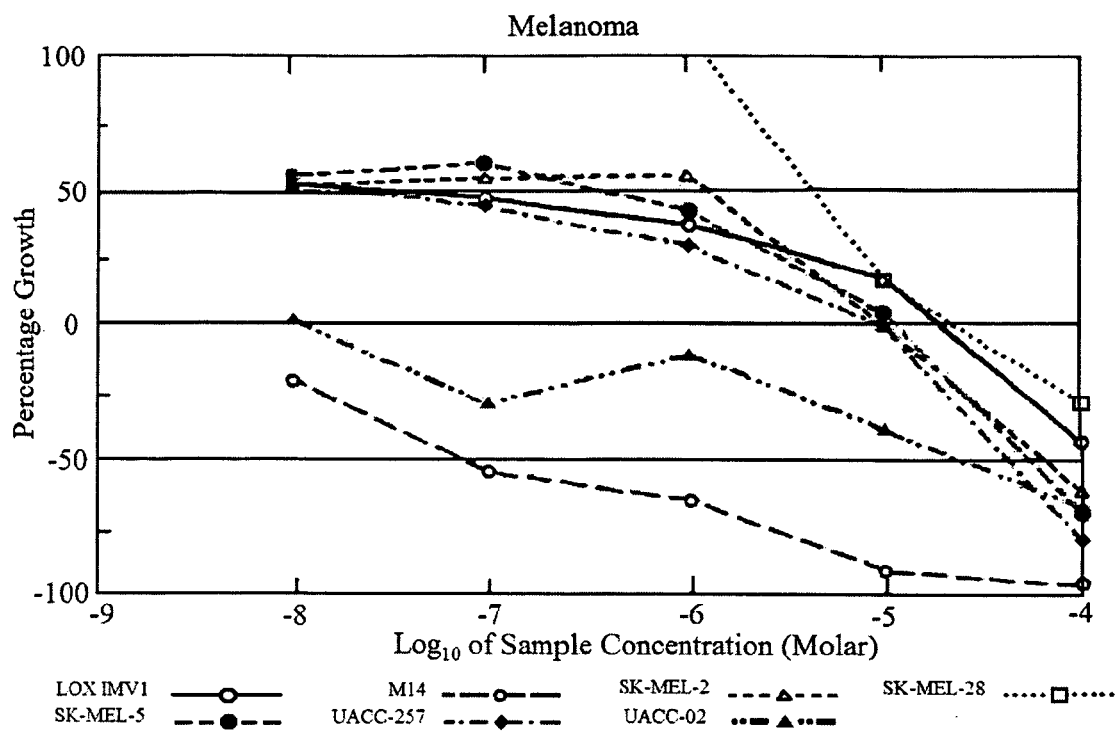
FIG. 7 is a graph showing National Cancer Institute (NCI) Developmental Therapeutics Program Dose Response Curves for Melanoma cell lines tested for Palmerolide A.
Figure 8:
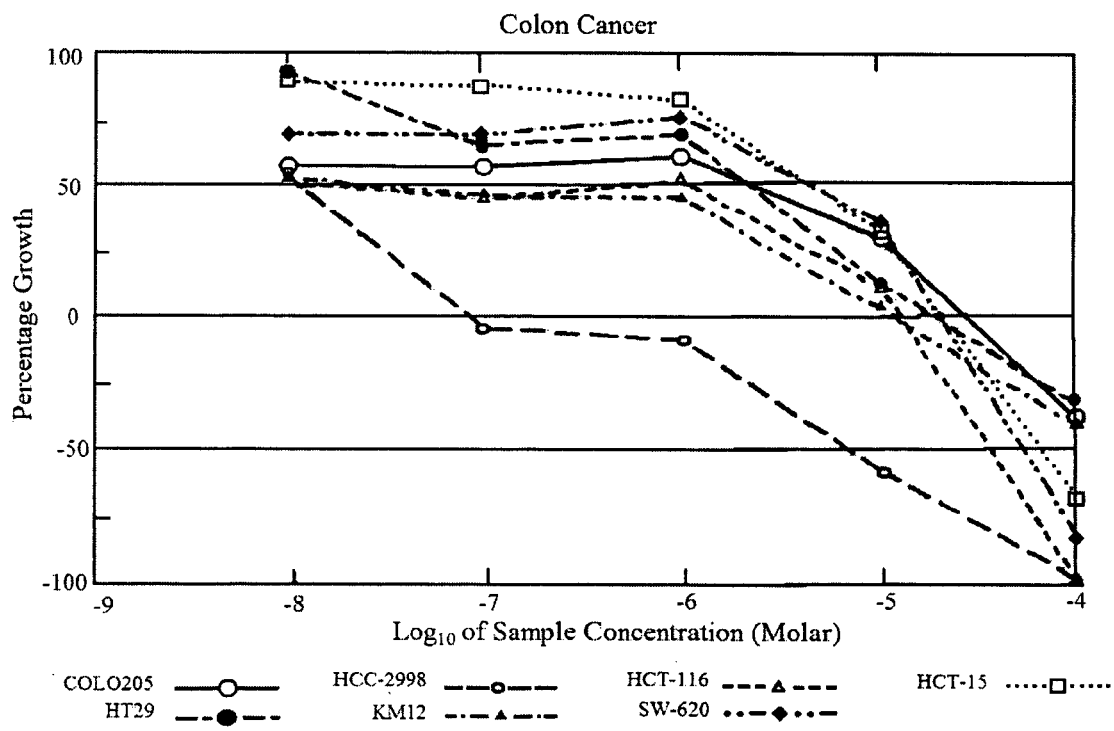
FIG. 8 is a graph showing National Cancer Institute (NCI) Developmental Therapeutics Program Dose Response Curves for Colon Cancer cell lines tested for Palmerolide A.
Figure 9:
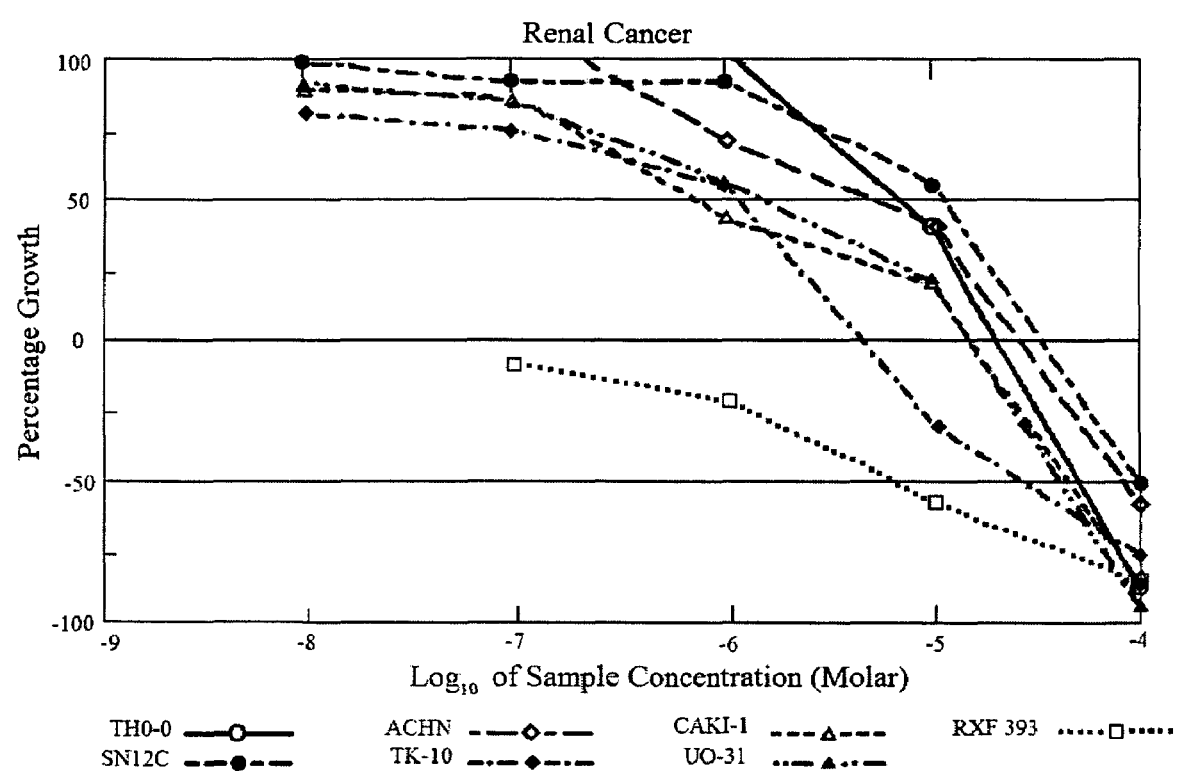
FIG. 9 is a graph showing National Cancer Institute (NCI) Developmental Therapeutics Program Dose Response Curves for Renal Cancer cell lines tested for Palmerolide A.

FIGS. 4 and 5, indicate the National Cancer Institutes Developmental Therapeutics Program In-Vitro Testing Results for Palmerolide A. FIG. 6 shows the National Cancer Institute (NCI) Developmental Therapeutics Program Dose Response Curves for all cell lines tested for Palmerolide A. In comparison, individual results are shown for Melanoma (FIG. 7), Colon Cancer (FIG. 8) and Renal Cancer (FIG. 9).

Example IV

Cytotoxicity of Palmerolide C

Figure 10:
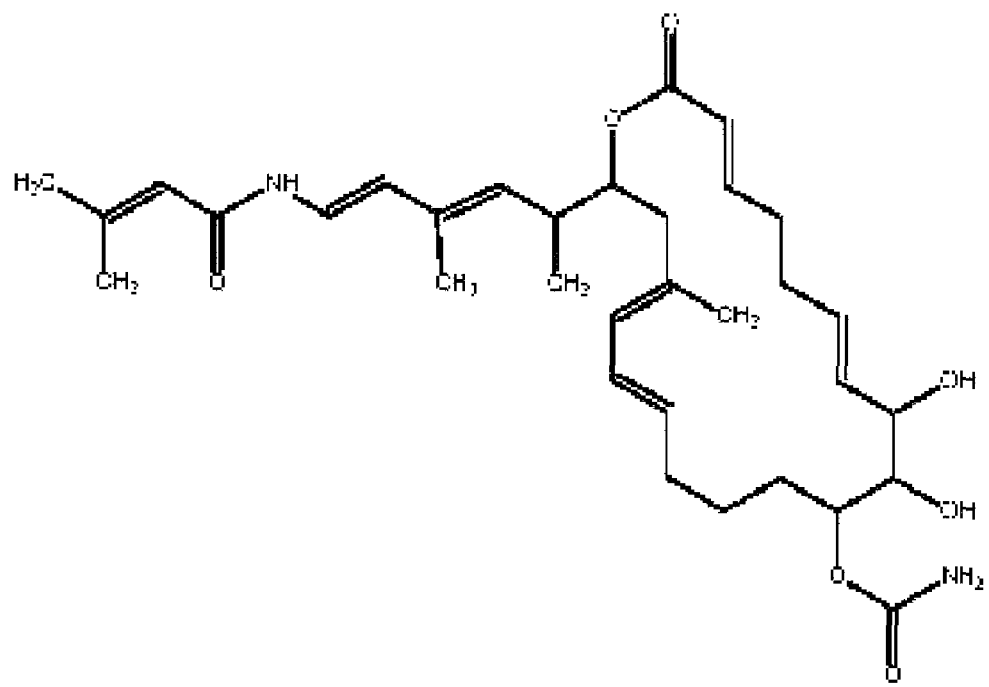
FIG. 10 is perspective view of the chemical formula for Palmerolide C.
Figure 14:
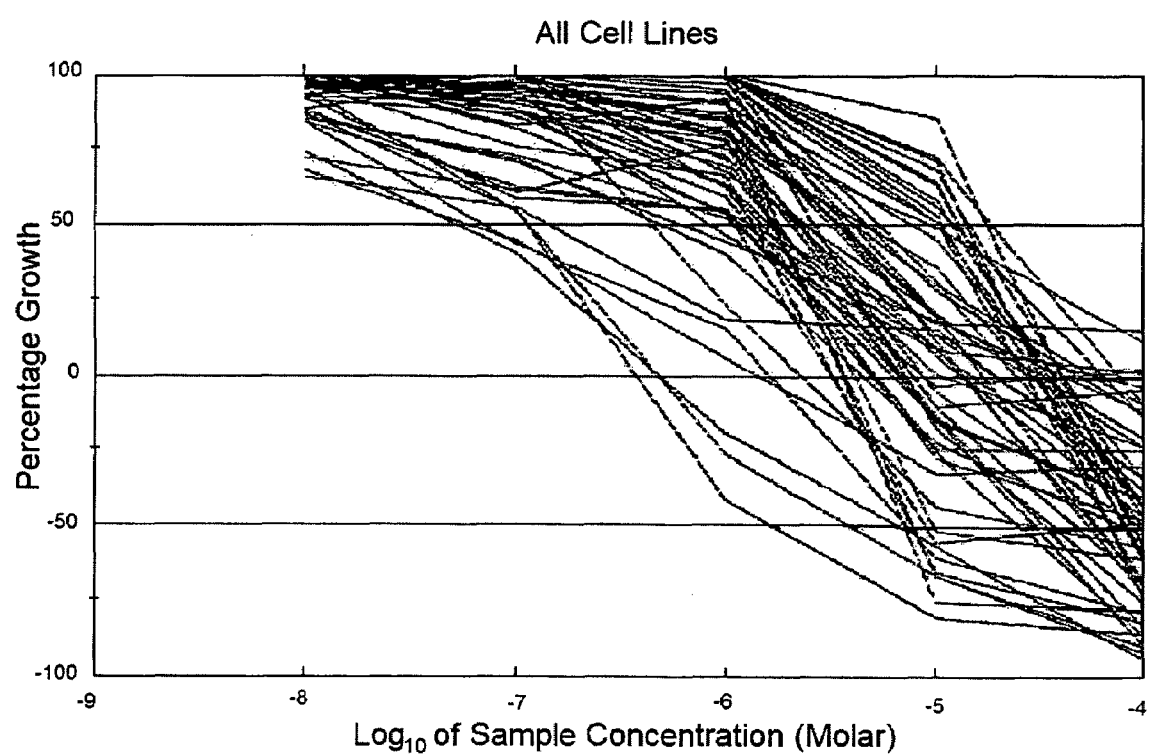
FIG. 14 is a graph showing National Cancer Institute (NCI) Developmental Therapeutics Program Dose Response Curves for all cell lines tested for Palmerolide C.

Palmerolide C, shown below and in FIG. 10, has the chemical formula C33H49N2O7 (for NMR data see FIG. 11). NCI cytotoxicity is shown in FIG. 12 and FIG. 13. NCI Dose Response Curves for all cell lines are presented in FIG. 14.

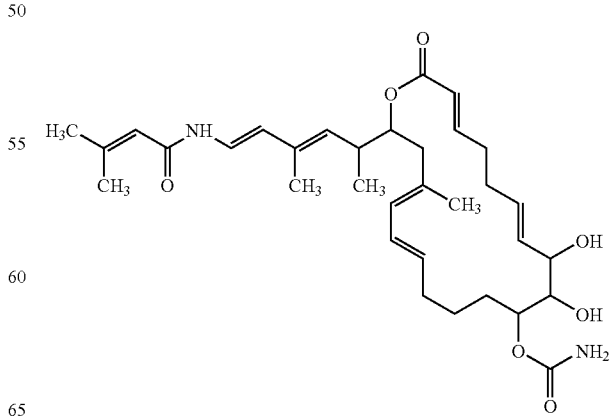

Example V

Cytotoxicity of Palmerolide D

Figure 15:
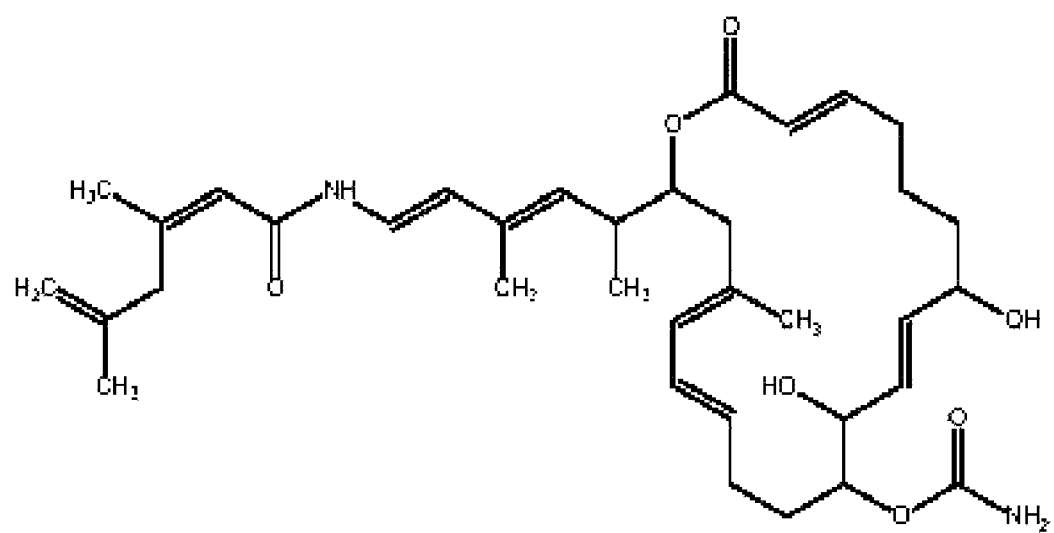
FIG. 15 is a perspective view of the chemical formula for Palmerolide D.

Palmerolide D, shown below and in FIG. 15, has the chemical formula C36H53N2O7. Palmerolide D NMR Data is shown in FIG. 16.

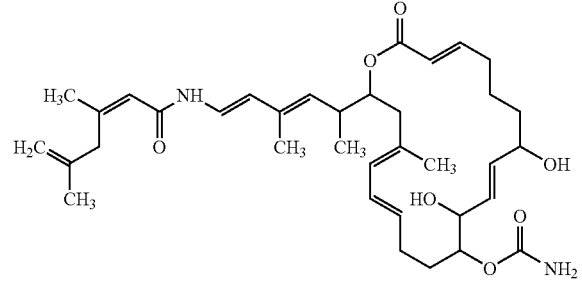

Example VI

Cytotoxicity of Palmerolide E

Figures 17, 18:
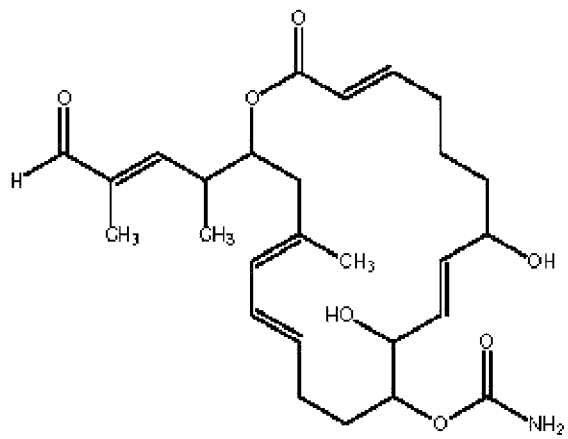
FIG. 17 is a perspective view of the chemical formula for Palmerolide E.
Figure 21:
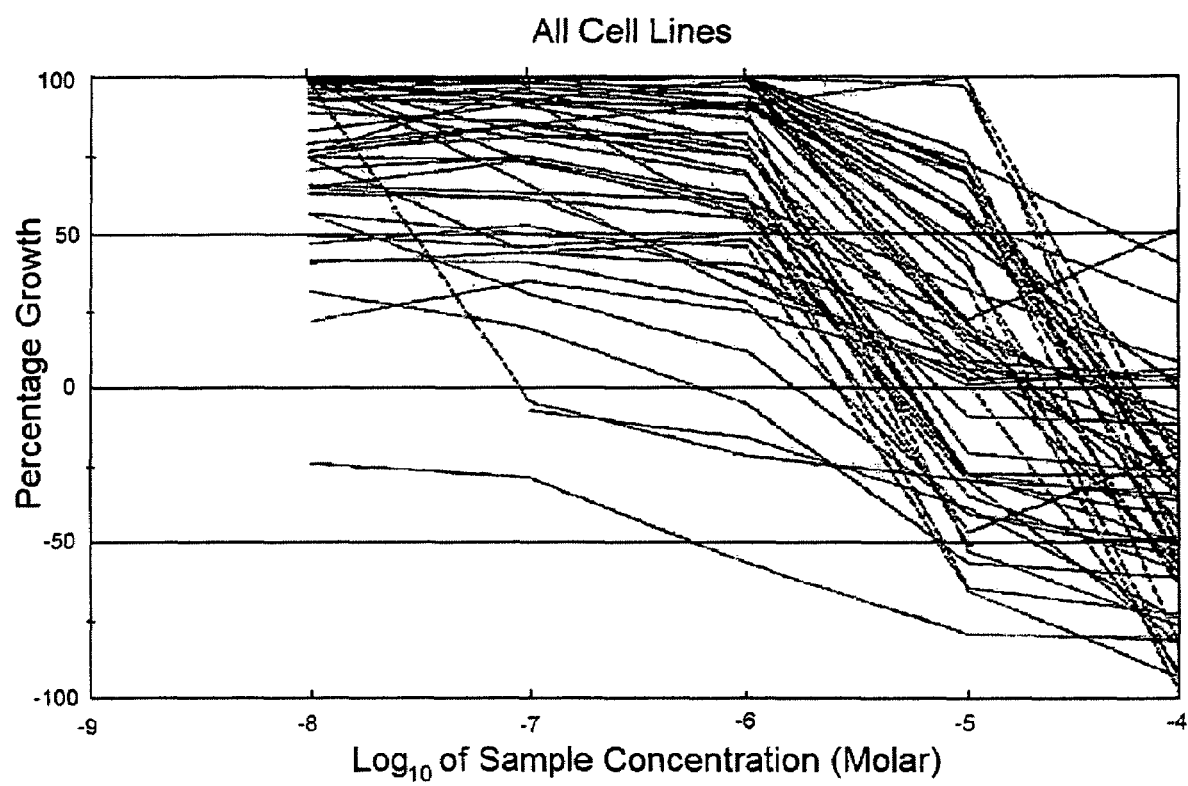

Palmerolide E, shown below and in FIG. 17, has the chemical formula C27H39NO7 (for NMR data see FIG. 18). NCI cytotoxicity is shown in FIG. 19 and FIG. 20. NCI Dose Response Curves for all cell lines are presented in FIG. 21.

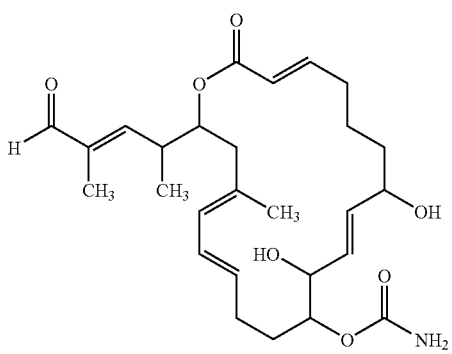

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be the to fall therebetween. Now that the invention has been described,

What is claimed is:

1. A composition comprising an isolated compound of formula I or racemic mixture thereof, or a pharmaceutically acceptable salt thereof, of the formula:

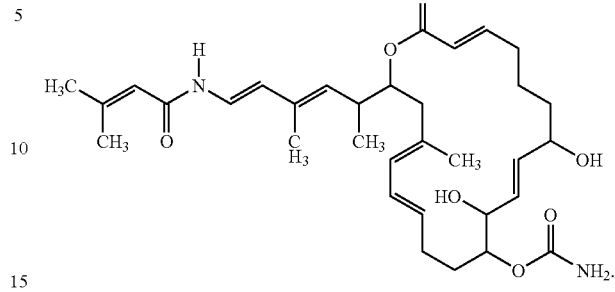

2. The composition of claim 1, wherein said composition further comprises a pharmaceutically acceptable carrier.

3. A composition comprising an isolated compound of formula II or a pharmaceutically acceptable salt thereof, of the formula:

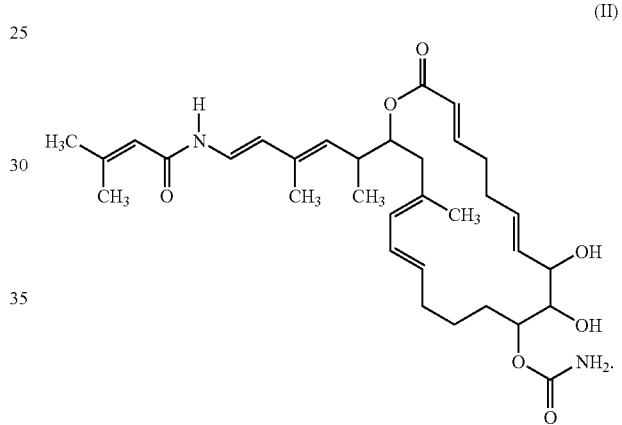

4. The composition of claim 3, wherein said composition further comprises a pharmaceutically acceptable carrier.

5. A composition comprising an isolated compound of formula III or a pharmaceutically acceptable salt thereof of the formula:

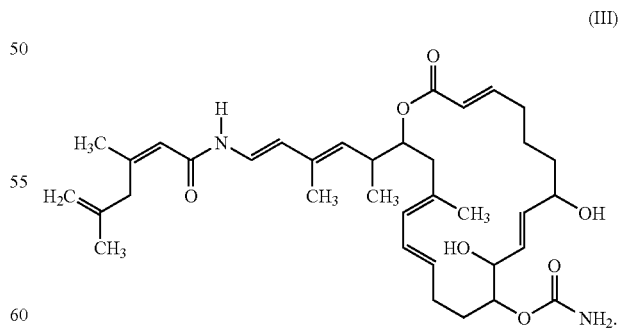

6. The composition of claim 5, wherein said composition further comprises a pharmaceutically acceptable carrier.

7. A composition comprising an isolated compound of formula IV or a pharmaceutically acceptable salt thereof, of the formula:

(IV)

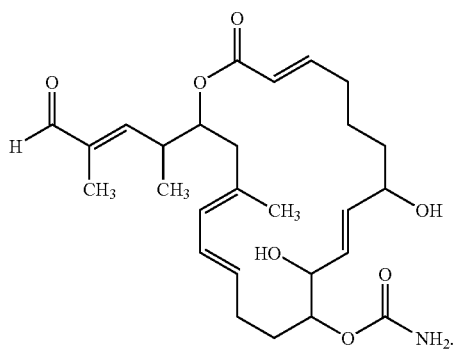

8. The composition of claim 7, wherein said composition further comprises a pharmaceutically acceptable carrier.

9. The composition of claim 1, wherein said salt is an acid salt of acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxy-ethane-sulfonate, lactate, maleate, methanesulfonate, 2-naphthalenesulfonate, nicotinate, oxalate, thiocyanate, tosylate or undecanoate.

10. The composition of claim 1, wherein said salt is a base salt of ammonium salts, alkali metal salts, alkaline earth metal salts, salts with organic bases, N-methyl-D-glucamine, or salts with amino acids.

11. The composition of claim 3, wherein said salt is an acid salt of acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxy-ethane-sulfonate, lactate, maleate, methanesulfonate, 2-naphthalenesulfonate, nicotinate, oxalate, thiocyanate, tosylate or undecanoate.

12. The composition of claim 3, wherein said salt is a base salt of ammonium salts, alkali metal salts, alkaline earth metal salts, salts with organic bases, N-methyl-D-glucamine, or salts with amino acids.

13. The composition of claim 5, wherein said salt is an acid salt of acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxy-ethane-sulfonate, lactate, maleate, methanesulfonate, 2-naphthalenesulfonate, nicotinate, oxalate, thiocyanate, tosylate or undecanoate.

14. The composition of claim 5, wherein said salt is a base salt of ammonium salts, alkali metal salts, alkaline earth metal salts, salts with organic bases, N-methyl-D-glucamine, or salts with amino acids.

15. The composition of claim 7, wherein said salt is an acid salt of acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxy-ethane-sulfonate, lactate, maleate, methanesulfonate, 2-naphthalenesulfonate, nicotinate, oxalate, thiocyanate, tosylate or undecanoate.

16. The composition of claim 7, wherein said salt is a base salt of ammonium salts, alkali metal salts, alkaline earth metal salts, salts with organic bases, N-methyl-D-glucamine, or salts with amino acids.

17. A purified compound, or a pharmaceutically acceptable salt thereof, having the formula selected from:

(I)

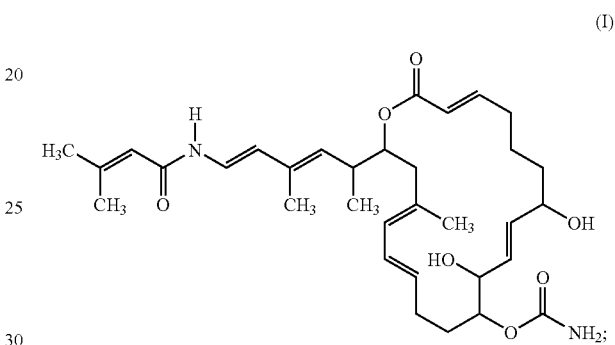

(II)

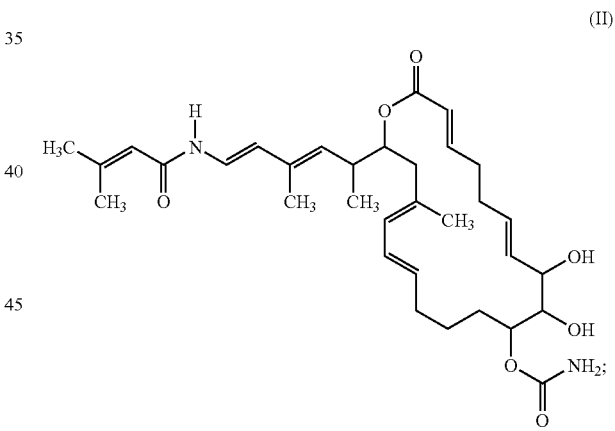

(III)

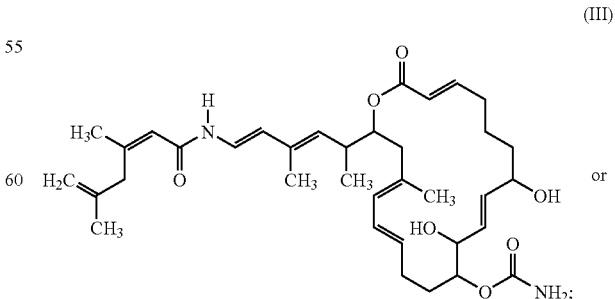

or

-continued

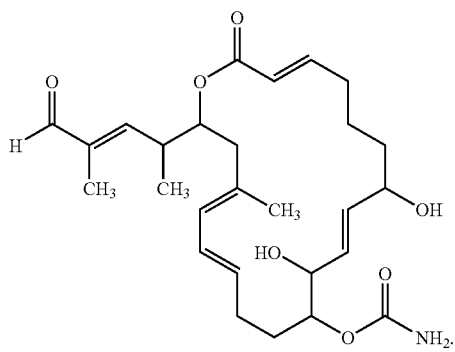

(IV)

18. The compound of claim 17, wherein said salt is an acid salt of acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate or undecanoate.

19. The compound of claim 17, wherein said salt is a base salt of ammonium salts, alkali metal salts, alkaline earth metal salts, salts with organic bases, N-methyl-D-glucamine, or salts with amino acids.

* * * * *

UNITED STATES PATENT AND TRADEMARK OFFICE
CERTIFICATE OF CORRECTION

PATENT NO. : 7,625,885 B2                                          Page 1 of 1
APPLICATION NO. : 10/906386
DATED         : December 1, 2009
INVENTOR(S)   : Bill J. Baker et al.

It is certified that error appears in the above-identified patent and that said Letters Patent is hereby corrected as shown below:

Column 11,
Line 18, "(C-1)" should read --(C-1')--.

Line 19, "C-5" should read --C-5'--.

Line 29, "C-5" should read --C-5'--.

Column 13,
Line 66, "formula I or racemic mixture thereof, or a" should read --formula I or a--.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO.         : 7,625,885 B2                                            Page 1 of 1
APPLICATION NO.    : 10/906386
DATED              : December 1, 2009
INVENTOR(S)        : Bill J. Baker et al.

It is certified that error appears in the above-identified patent and that said Letters Patent is hereby corrected as shown below:

Title Page, Item (75) Inventors:

"Thusahara" should read --Thushara--.

Signed and Sealed this

Sixteenth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,625,885 B2  Page 1 of 1
APPLICATION NO. : 10/906386
DATED : December 1, 2009
INVENTOR(S) : Baker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this

Second Day of November, 2010

David J. Kappos
*Director of the United States Patent and Trademark Office*